US00PP08742P

United States Patent [19]

Laver

[11] Patent Number: Plant 8,742

[45] Date of Patent: May 24, 1994

[54] ROSE PLANT LAVAWAY

[75] Inventor: Keith G. Laver, Caledon, Canada

[73] Assignee: Bear Creek Gardens, Inc., Medford, Oreg.

[21] Appl. No.: 971,324

[22] Filed: Nov. 4, 1992

[51] Int. Cl.[5] ..... A01H 5/00

[52] U.S. Cl. ..... Plt./8.1

[58] Field of Search ..... Plt. 8.1, 3, 7.1, 8.2

[56] References Cited

U.S. PATENT DOCUMENTS

PLT 6514 1/1989 Warriner ..... Plt. 8.1

*Primary Examiner*—Howard J. Locker
*Assistant Examiner*—Erich Veitenheimer
*Attorney, Agent, or Firm*—Klarquist Sparkman Campbell Leigh & Whinston

[57] ABSTRACT

A miniature rose plant having a compact, attractive growth habit; ease of propagation from softwood cutting; production of an abundance of near-white blooms in 4-inch pots in a greenhouse or outside in the garden, and the ability to be forced in a greenhouse to bloom in 5 to 7 weeks from softwood cuttings.

1 Drawing Sheet

1

The present invention relates to a new and distinct variety of rose plant of the miniature class which was originated by me by crossing the variety Tabris with the variety June Laver.

The primary objective of this breeding was to produce a new rose variety having a low, compact growth habit and suitability for pot forcing. The objective was substantially achieved along with other desirable improvements as evidenced by the following unique combination of characteristics which are outstanding in the new variety and which distinguish it from its parents, as well as from all other varieties of which I am aware:

1. Compact, attractive growth habit;
2. Easy to propagate from softwood cutting;
3. Produces an abundance of near-white blooms in 4-inch pots in a greenhouse or outside in the garden; and
4. Can be forced in a greenhouse to bloom in 5 to 7 weeks from softwood cuttings.

Asexual reproduction of this new variety by softwood cuttings, as performed at Wasco and Somis, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Tabris.

*Pollen parent.*—June Laver.

Classification:

*Botanical.*—Rosa hybrida.

*Commerical.*—Miniature.

FLOWER

Observations made from specimens grown in a greenhouse environment in Somis, Calif., in 1992.

Blooming habit: Recurrent.

Bud:

2

*Size.*—½ inch long when the petals start to unfurl.

*Form.*—Short, pointed ovoid.

*Color.*—When sepals first divide, bud color is Yellow White Group 158C. When half blown, the upper and lower sides of the petals are Yellow White Group 158C.

*Sepals.*—Color: Green Group 138B. Surface texture: Covered in fine hairs. There are three lightly appendaged sepals. There are two unappendaged sepals with hairy edges.

*Receptacle.*—Color: Yellow Green Group 146A. Shape: Funnel. Size: Large (¼ inch wide×3/16 inch long). Surface: Smooth.

*Peduncle.*—Length: Short (¾×1 inch). Surface: Smooth. Color: Light green. Strength: Stiff, erect.

Bloom:

*Size.*—Small. Average open size is 1¾ to 2 inches in diameter.

*Borne.*—Singly and several together, in clusters. If in clusters: Rounded with 2 to 5 flowers.

*Stems.*—Short, strong (4 to 5 inches).

*Form.*—When first open: High centered. Permanence: Flattens, all petals curl and quill.

*Petalage.*—Number of petals under normal conditions: 40 to 50.

*Color.*—The upper and reverse sides of the petals are Yellow White Group 158C. The bases of petals have a small yellow half moon at the point of attachment. The major color on the upper side is Yellow White Group 158C.

*Variegations.*—None.

*Discoloration.*—No change in general tonality at the end of the first day or at the end of the third day.

*Frangrance.*—Slight.

Petals:

*Texture.*—Medium.

*Shape.*—Deltoid.

*Form.*—Tips slightly recurved and edges moderately quilled.

*Arrangement.*—Imbricated, with few petaloids in the center.

*Persistence.*—Hang on and dry.

*Lastingness.*—On the plant: Long (6 days). As a cut flower: Not tested.

Reproductive parts:

*Anthers.*—Size: Medium. Quantity: Few. Color: Yellow. Arrangement: Regular around styles, mixed with petaloids.

*Filaments.*—Color: Yellow.

*Pollen.*—Color: Lemon yellow.

*Styles.*—Color: Yellow.

*Stigmas.*—Color: Greenish white.

Form: Bush.

Gorwth: Vigorous, dwarf, branching, compact. Mature height will vary from 6 to 8 inches and width from 8 to 10 inches.

Foliage: Number of leaflets on norman mid-stem leaves: 5.

*Size.*—Small (3×2 inches).

*Quantity.*—Abundant.

*Color.*—New foliage: Light green. Old foliage: Upper surface: Green Group 137A. Lower surface: Green Group 138B.

Leaflets:

*Shape.*—Pointed oval.

*Texture.*—Upper side: Smooth.

*Edge.*—Serrated.

*Serration.*—Single, small.

*Petiole rachis.*—Color: Green.

*Petiole underside.*—Smooth, with occasional prickles.

*Stipules.*—Short, serrated.

*Disease resistance.*—Resistant to mildew under normal growing conditions at Somis, Calif.

Wood:

*New wood.*—Color: Light green. Bark: Smooth.

*Old wood.*—Color: Green. Bark: Smooth.

Prickles:

*Quantity.*—On main canes from base and on laterals from main canes: ordinary.

*Form.*—Short, straight.

*Color when young.*—Transparent.

Small prickles:

*Quantity.*—On main stalks and on laterals: Few.

*Color.*—Green.

I claim:

1. A new and distinct variety of rose plant of the miniature class, substantially as herein shown and described, characterized particularly as to novelty by the unique combination of its compact, attractive growth habit; ease of propagation from softwood cutting; production of an abundance of near-white blooms in 4-inch pots in a greenhouse or outside in the garden, and the ability to be forced in a greenhouse to bloom in 5 to 7 weeks from softwood cuttings.

* * * * *

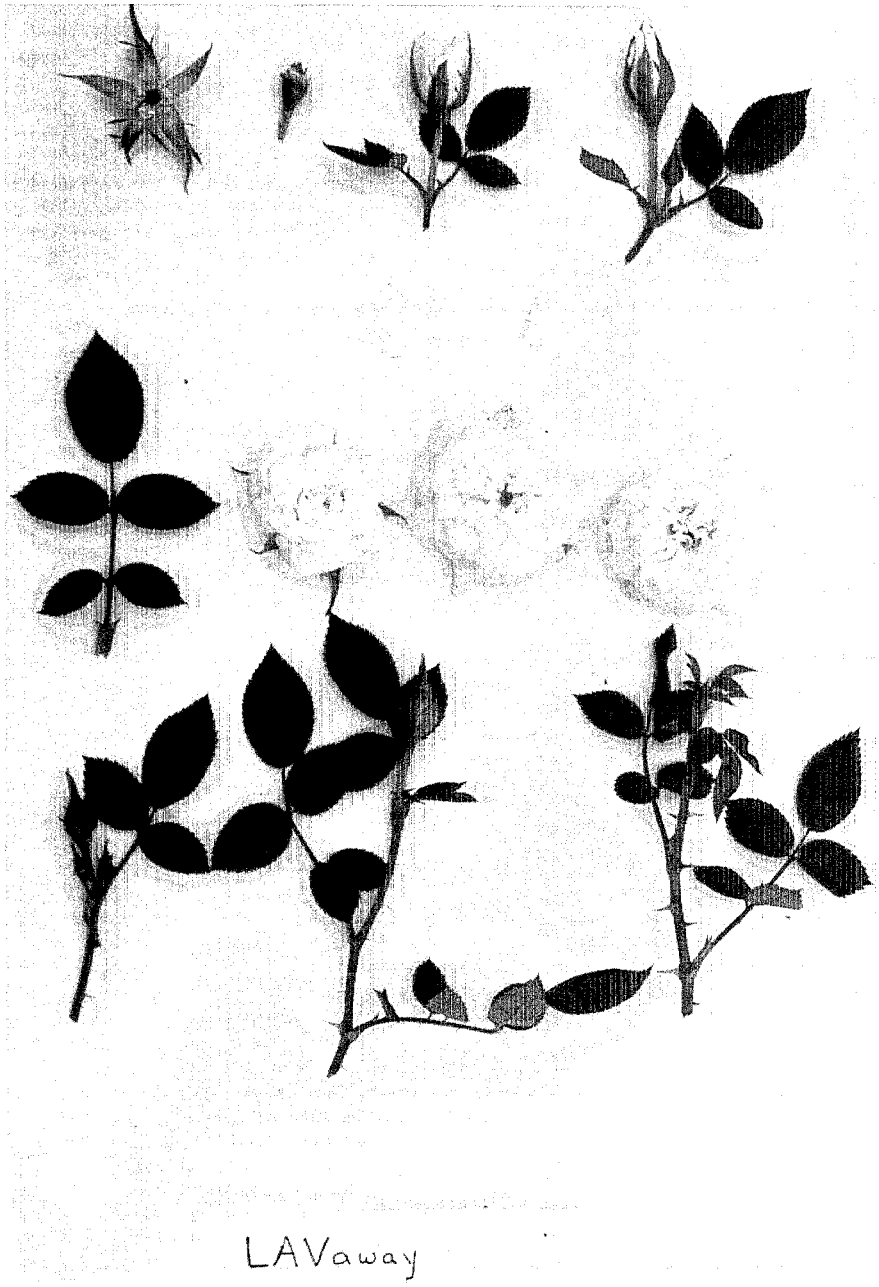
LAVaway